United States Patent
Dhiraj et al.

(10) Patent No.: US 9,822,164 B2
(45) Date of Patent: Nov. 21, 2017

(54) LABELLING AGENT, AND COMPOSITION FOR LABELLING A PROTEIN, METHOD FOR LABELLING A PROTEIN, AND METHOD FOR DETECTING A PROTEIN

(71) Applicant: KOREA INSTITUTE OF SCIENCE AND TECHNOLOGY, Seoul (KR)

(72) Inventors: Murale Dhiraj, Seoul (KR); Seong Cheol Hong, Seoul (KR); Ji Hyeon Yun, Seoul (KR); Chang No Yoon, Seoul (KR); Jun Seok Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 13 days.

(21) Appl. No.: 14/927,942

(22) Filed: Oct. 30, 2015

(65) Prior Publication Data
US 2016/0121293 A1    May 5, 2016

(30) Foreign Application Priority Data
Oct. 31, 2014 (KR) ........................ 10-2014-0150621

(51) Int. Cl.
| | | |
|---|---|---|
| C07K 14/765 | (2006.01) |
| C07D 263/57 | (2006.01) |
| C07D 277/66 | (2006.01) |
| C07D 235/12 | (2006.01) |
| C07D 235/14 | (2006.01) |

(52) U.S. Cl.
CPC .......... *C07K 14/765* (2013.01); *C07D 235/12* (2013.01); *C07D 235/14* (2013.01); *C07D 263/57* (2013.01); *C07D 277/66* (2013.01)

(58) Field of Classification Search
None
See application file for complete search history.

(56) References Cited

PUBLICATIONS

Hunter et al. "139. The associating effect of the hydrogen atom. Part VIII. The N—H—N bond. Benziminazoles, glyoxalines, amidines, and guanidines" Journal of the Chemical Society, 1941, pp. 777-786.*

Rogembusch et al., Synthesis and spectroscopic characterisation of new ESIPT fluorescent protein probes, Photochem. photobiol. Sci., Jan. 20, 2005, pp. 254-259, 2005 4.

A communication from Korean Intellectual Property Office dated Dec. 9, 2015 of Korean Patent Application No. 10-2014-0150621, which corresponds to present application.

* cited by examiner

*Primary Examiner* — Joseph Kosack
(74) *Attorney, Agent, or Firm* — Goldilocks Zone IP Law

(57) ABSTRACT

Provided are a labelling agent including a compound of the following Formula 1, a labelling composition, a method of labelling a protein with the labelling agent, and a method of detecting the protein using the labelling agent:

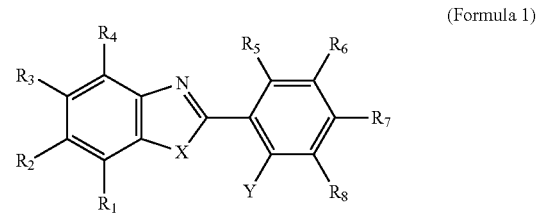

(Formula 1)

wherein $R_1$, $R_2$, $R_3$, $R_4$, $R_5$, $R_6$, and $R_8$ are independently H, substituted or unsubstituted —$C_{1-10}$-alkyl-, —$C_{2-10}$-alkenyl, or —$C_{2-10}$-alkynyl, $R_7$ is H or —$NR_9R_{10}$, $R_9$ and $R_{10}$ are independently H, substituted or unsubstituted —$C_{1-10}$-alkyl-, —$C_{2-10}$-alkenyl, or —$C_{2-10}$-alkynyl, X is —$NR_{11}$, —O, or S, $R_{11}$ is H, substituted or unsubstituted —$C_{1-10}$-alkyl-, —$C_{2-10}$-alkenyl, or —$C_{2-10}$-alkynyl, Y is —$OR_{12}$ or —$NR_{13}R_{14}$, $R_{12}$ is H, substituted or unsubstituted —$C_{1-10}$-alkyl-, —$C_{2-10}$-alkenyl, or —$C_{2-10}$-alkynyl, and $R_{13}$ and $R_{14}$ are independently H, substituted or unsubstituted —$C_{1-10}$-alkyl-, —$C_{2-10}$-alkenyl, or —$C_{2-10}$-alkynyl.

5 Claims, 4 Drawing Sheets

LABELLING AGENT, AND COMPOSITION FOR LABELLING A PROTEIN, METHOD FOR LABELLING A PROTEIN, AND METHOD FOR DETECTING A PROTEIN

CROSS-REFERENCE TO RELATED APPLICATION

This application claims the benefit of Korean Patent Application No. 10-2014-0150621, filed on Oct. 31, 2014, in the Korean Intellectual Property Office, the disclosure of which is incorporated herein in its entirety by reference.

BACKGROUND

1. Field

The present disclosure relates to a labelling agent, a composition for labelling a protein, a method of labelling a protein using the labelling agent, and a method of detecting a protein.

2. Description of the Related Art

A technology of labelling in vivo proteins is one of fields which are of great importance in molecular biology, since development of green fluorescence protein (GFP). This technology is used to monitor protein migration according to cell proliferation and signal transduction as well as location of proteins present in an organism, and thus has a great function to overcome resolution of the existing microscopes and to find out a new mechanism.

To label proteins with GFP, transfection using virus is widely used. However, since virus has a feature of random integration of viral DNA into host genome, there is a concern about genetic mutation.

To overcome this problem, a labelling method of directly attaching a small molecule having fluorescence to a target protein has been studied. However, this method also has a problem of bio-orthogonality due to reaction of a binding site of the small molecule with other functional groups in the organism. Recently, studies have been conducted on a method of labelling proteins without reaction with functional groups in the organism, such as click chemistry, or a method of using photocrosslinking.

SUMMARY

An aspect provides a labelling agent.
Another aspect provides a composition for labelling.
Still another aspect provides a method of labelling a protein.
Still another aspect provides a method of detecting a protein.

Advantageous Effect

A labelling agent according to an aspect may be used to efficiently label a protein.

A composition for labelling according to another aspect may be used to efficiently label a protein.

A method of labelling the protein according to still another aspect may be used to efficiently label a protein.

A method of detecting the protein according to still another aspect may be used to efficiently detect a protein.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
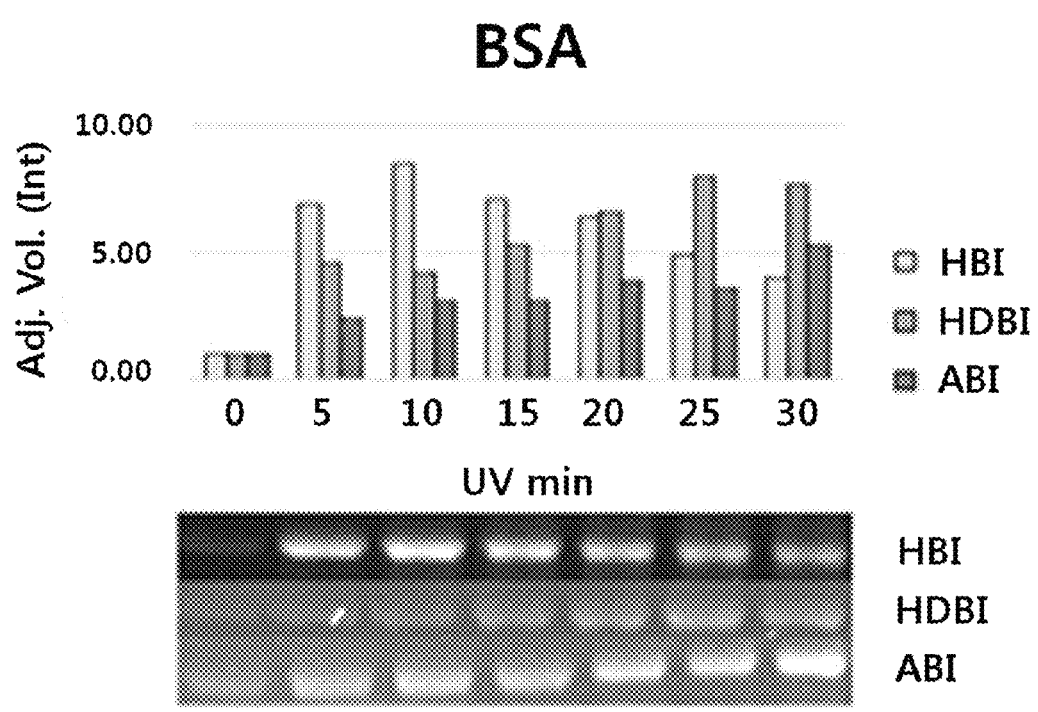
FIGS. 1a through 1d show labeling of BSA, HAS, peroxidase, and lysozyme proteins with HBI, HDBI, and HBO among compounds and their labelling efficiency according to ultraviolet (UV) irradiation time.

An aspect provides a labelling agent represented by the following Chemical Formula 1:

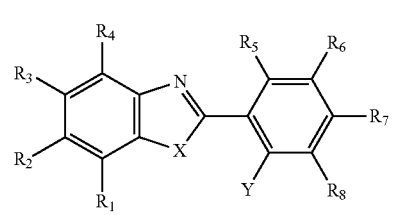

(Formula 1)

wherein $R_1$, $R_2$, $R_3$, $R_4$, $R_5$, $R_6$, and $R_8$ may be independently H, substituted or unsubstituted —$C_{1-10}$-alkyl-, —$C_{2-10}$-alkenyl, or —$C_{2-10}$-alkynyl, $R_7$ may be H or —$NR_9R_{10}$, $R_9$ and $R_{10}$ may be independently H, substituted or unsubstituted —$C_{1-10}$-alkyl-, —$C_{2-10}$-alkenyl, or —$C_{2-10}$-alkynyl, X may be —$NR_{11}$, —O, or S, $R_{11}$ may be H, substituted or unsubstituted —$C_{1-10}$-alkyl-, —$C_{2-10}$-alkenyl, or —$C_{2-10}$-alkynyl, and Y may be —$OR_{12}$ or —$NR_{13}R_{14}$, $R_{12}$ may be H, substituted or unsubstituted —$C_{1-10}$-alkyl-, —$C_{2-10}$-alkenyl, or —$C_{2-10}$-alkynyl, $R_{13}$ and $R_{14}$ may be independently H, substituted or unsubstituted —$C_{1-10}$-alkyl-, —$C_{2-10}$-alkenyl, or —$C_{2-10}$-alkynyl.

In a specific embodiment, $R_1$, $R_2$, $R_3$, $R_4$, $R_5$, $R_6$, and $R_8$ may be independently H, substituted or unsubstituted —$C_{1-10}$-alkyl-, $R_7$ may be H or —$NR_9R_{10}$, $R_9$ and $R_{10}$ may be independently H, substituted or unsubstituted —$C_{1-10}$-alkyl-, $R_{11}$ may be H, substituted or unsubstituted —$C_{1-10}$-alkyl-, and $R_{12}$ may be H, substituted or unsubstituted —$C_{1-10}$-alkyl-, $R_{13}$ and $R_{14}$ may be independently H, substituted or unsubstituted —$C_{1-10}$-alkyl-.

In a specific embodiment, the compound may be selected from the group

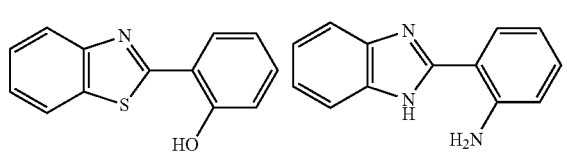

consisting of

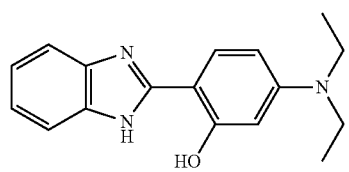

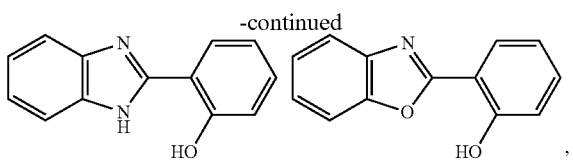

and combinations thereof.

In a specific embodiment, the compound represented by Formula 1 may be selected from the group consisting of 2-(2-hydroxyphenyl)benzothiazole (HBT), 2-(2-hydroxyphenyl)benzimidazole (HBI), 2-(2-hydroxyphenyl)-5-(diethylamino)benzimidazole (HDBI), 2-(2-hydroxyphenyl)benzoxazole (HBO), 2-(2-Aminophenyl)-1H-benzimidazole, and combinations thereof.

The term "alkyl" refers to a straight or branched chain, saturated monovalent aliphatic hydrocarbon group. Unless otherwise defined, the alkyl group may generally include 1~10, 1~8, 1~6, 1~4 or 1~3 carbon atoms. Examples of the alkyl group may include methyl, ethyl, propyl (e.g., n-propyl and isopropyl), butyl (e.g., n-butyl, isobutyl, t-butyl, sec-butyl), pentyl (e.g., n-pentyl, isopentyl, and neopentyl), n-hexyl, n-heptyl, n-octyl, n-nonyl and n-decyl.

The term "alkenyl refers to a straight or branched chain, unsaturated monovalent hydrocarbon group having one or more carbon-carbon double bonds. Unless otherwise defined, the alkenyl group may generally include 2~10, 2~8, 2~6, 2~4 or 2~3 carbon atoms. Examples of the alkenyl group may include ethenyl, n-propenyl, isopropenyl, n-but-2-enyl, cyclohexenyl, or n-hex-3-enyl. The alkenyl may include cis and trans isomers or a mixture thereof.

The term "alkynyl" refers to a straight or branched chain, unsaturated monovalent hydrocarbon group having one or more carbon-carbon triple bonds. Unless otherwise defined, the alkynyl group may generally include 2~10, 2~8, 2~6, 2~4 or 2~3 carbon atoms. Examples of the alkynyl group may include ethinyl, n-propynyl, n-but-2-ynyl, and or n-hex-3-ynyl.

The substituted alkyl group refers to an alkyl group having 1~5 substituents, which are selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, and in which substituent is the same as defined herein.

"Alkoxy" refers to an —O-alkyl group in which alkyl is defined herein. Examples of the alkoxy may include methoxy, ethoxy, n-propoxy, isopropoxy, n-butoxy, t-butoxy, sec-butoxy, and n-pentoxy.

The term "aryl" refers to an aromatic hydrocarbon group having a single ring or multiple rings. The multiple rings may include rings having fused rings (e.g., naphthalene), and/or non-fused rings (e.g., biphenyl). The multiple rings may have, for example, 2, 3, or 4 rings. Unless otherwise defined, the aryl group may generally include 5 to 10, 6 to 15, 6 to 12, or 6 to 10 carbon atoms. Examples of the aryl group may include phenyl, naphthalenyl (e.g., naphthalen-1-yl and naphthalen-2-yl), biphenyl, anthracenyl, and phenanthrenyl.

The term "cycloalkyl" refers to a non-aromatic carbocycle containing cyclic alkyl, alkenyl and alkynyl groups. The cycloalkyl group may include a single ring or multiple rings. The multiple rings may have, for example, 2, 3 or 4 fused rings. Unless otherwise defined, the cycloalkyl may generally include 3 to 10, or 3 to 7 cyclic carbon atoms. Examples of the cycloalkyl group may include cyclopropyl, cyclobutyl, cyclopentyl, cyclohexyl, cycloheptyl, cyclohexadienyl, cycloheptatrienyl, norbornyl, norcarnyl, and adamantyl.

The term "heterocycloalkyl" refers to a non-aromatic heterocyclic ring containing heteroatoms forming rings of one or more atoms selected from N, O, and S. The heterocycloalkyl group may include a single ring or multiple rings, for example, 2, 3 or 4 fused rings. Examples of the heterocycloalkyl group may include morpholinyl, thiomorpholinyl, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isooxazolidinyl, isothiazolidinyl, pyrazolidinyl, oxazolidinyl, thiazolidinyl. Unless otherwise defined, the heterocycloalkyl may generally include 3 to 10, 3 to 7, 5 to 7, or 5 to 6 atoms forming rings.

The term "heteroaryl" refers to a monovalent aromatic group having one or more heteroatoms selected from N, O and S as a ring component. The heteroaryl may include a single ring or multiple rings. The multiple rings may have, for example, 2, 3 or 4 condensed rings. Unless otherwise defined, the heteroaryl may generally include 3 to 10, 3 to 7, or 3 to 5 cyclic atoms. The heteroaryl may generally include 1, 2 or 3 heteroatoms. Examples of the heteroaryl group may include pyridyl, N-oxopyridyl, pyrimidinyl, pyrazinyl, pyridazinyl, triazinyl, furyl, quinolyl, isoquinolyl, thienyl, imidazolyl, furanyl, thiazolyl, indolyl, pyril, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, benzimidazolyl, and indolynyl.

Definition of the substitution (substituted group) is as follows. The term "substituted" in the "substituted" alkyl group, alkoxy group, alkenyl group, alkynyl group, alkyleneoxide group, cycloalkyl group, aryloxy group, or heteroaryl group refers to substitution thereof with a hydroxy group, a nitro group, a cyano group, an amino group, an amidino group, a hydrazine, a hydrazone, a carboxyl group or a salt thereof, a substituted sulfonic acid group or a salt thereof, a phosphoric acid or a salt thereof, or a $C_{1-10}$ alkyl group, a $C_{1-10}$ alkoxy group, a $C_{2-10}$ alkenyl group, a $C_{2-10}$ alkynyl group, a $C_{1-10}$ heteroalkyl group, a $C_{6-10}$ aryl group, a $C_{6-10}$ arylalkyl group, a $C_{6-10}$ heteroaryl group, or a $C_{6-10}$ heteroarylalkyl group.

Specific examples of the $C_{1-10}$ alkyl group may include methyl, ethyl, propyl, isobutyl, sec-butyl, tert-butyl, neo-butyl, iso-amyl, and hexyl, and one or more hydrogen atoms of the alkyl group may be substituted with the substituents described above where the term "substituted" is defined.

Specific examples of the $C_{1-10}$ alkoxy group may include methoxy, ethoxy, and propoxy, and one or more hydrogen atoms of the alkoxy group may be substituted with the substituents described above where the term "substituted" is defined.

Specific examples of the $C_{2-10}$ alkenyl group may include vinylene and allylene, and one or more hydrogen atoms of the alkenyl group may be substituted with the substituents described above where the term "substituted" is defined.

Specific example of the $C_{2-10}$ alkynyl group may include acetylene, and one or more hydrogen atoms of the alkynyl group may be substituted with the substituents described above where the term "substituted" is defined.

Specific examples of the $C_{2-10}$ alkylene oxide group may include ethylene oxide, propylene oxide, and butylene oxide.

Specific examples of the $C_{3-10}$ cycloalkyl group may include cyclopropyl, cyclobutyl, cyclopentyl, and cyclohexyl, and one or more hydrogen atoms of the cycloalkyl group may be substituted with the substituents described above where the term "substituted" is defined.

The $C_{6-10}$ aryl group is used alone or in combination, and refers to an aromatic system having one or more rings. Examples thereof may include phenyl and naphthyl. Also, one or more hydrogen atoms of the aryl group may be substituted with the substituents described above where the term "substituted" is defined.

Example of the $C_{6-10}$ aryloxy group may include phenoxy, and one or more hydrogen atoms of the aryloxy group may be substituted with the substituents described above where the term "substituted" is defined.

The $C_{6-10}$ heteroaryl group refers to an organic compound that contains one or more heteroatoms selected from N, O, P, and S, and the remaining ring atoms are carbon atoms. Example of thereof may include pyridyl. Also, one or more hydrogen atoms of the heteroaryl group may be substituted with the substituents described above where the term "substituted" is defined.

The labelling agent may be used to label a protein. The labelling agent may be a protein labelling agent.

The labelling agent may be a fluorescent or light-absorbing labelling agent. The labelling agent may cause fluorescence or absorbance. The fluorescence may be blue or green fluorescence. When the labelling agent is irradiated with light, hydrogen atoms in the labelling agent move to neighboring oxygen or nitrogen atoms to emit fluorescence with large Stokes shift.

Another aspect provides a labelling composition including a compound of the following Formula 2 or 3 and a protein.

The compound of the following Formula 2 and the protein are as follows:

(Formula 2)

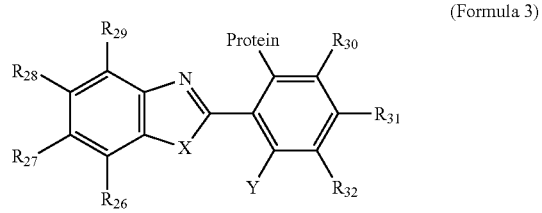

wherein $R_{15}$, $R_{16}$, $R_{17}$, $R_{18}$, $R_{19}$, $R_{20}$, and $R_{21}$ may be independently H, substituted or unsubstituted —$C_{1-10}$-alkyl-, —$C_{2-10}$-alkenyl, or —$C_{2-10}$-alkynyl, X may be —$NR_{22}H$, —O, or S, $R_{22}$ may be H, substituted or unsubstituted —$C_{1-10}$-alkyl-, —$C_{2-10}$-alkenyl, or —$C_{2-10}$-alkynyl, Y may be —$OR_{23}$ or —$NR_{24}R_{25}$, $R_{23}$ may be H, substituted or unsubstituted —$C_{1-10}$-alkyl-, —$C_{2-10}$-alkenyl, or —$C_{2-10}$-alkynyl, and $R_{24}$ and $R_{25}$ may be independently H, substituted or unsubstituted —$C_{1-10}$-alkyl-, —$C_{2-10}$-alkenyl, or —$C_{2-10}$-alkynyl.

The compound of the following Formula 3 and the protein are as follows:

(Formula 3)

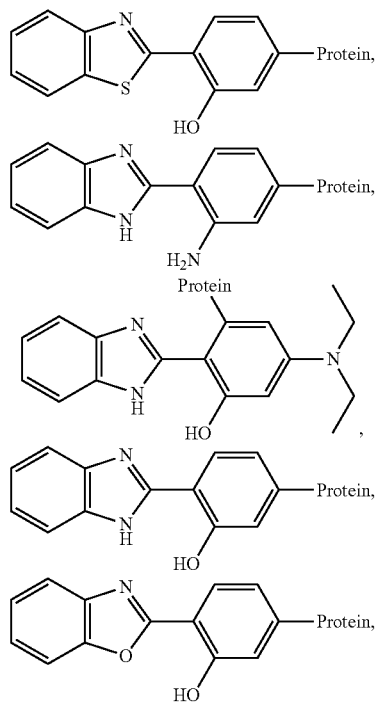

wherein $R_{26}$, $R_{27}$, $R_{28}$, $R_{29}$, $R_{30}$, and $R_{32}$ may be independently H, substituted or unsubstituted —$C_{1-10}$-alkyl-, —$C_{2-10}$-alkenyl, or —$C_{2-10}$-alkynyl, $R_{31}$ may be —$NR_{32}R_{33}$, $R_{32}$ and $R_{33}$ may be independently H, substituted or unsubstituted —$C_{1-10}$-alkyl-, —$C_{2-10}$-alkenyl, or —$C_{2-10}$-alkynyl, X may be —$NR_{34}H$, —O, or S, $R_{34}$ may be H, substituted or unsubstituted —$C_{1-10}$-alkyl-, —$C_{2-10}$-alkenyl, or —$C_{2-10}$-alkynyl, Y may be —$CR_{35}$ or —$NR_{36}R_{37}$, $R_{35}$ may be H, substituted or unsubstituted —$C_{1-10}$-alkyl-, —$C_{2-10}$-alkenyl, or —$C_{2-10}$-alkynyl, and $R_{36}$ and $R_{37}$ may be independently H, substituted or unsubstituted —$C_{1-10}$-alkyl-, —$C_{2-10}$-alkenyl, or —$C_{2-10}$-alkynyl.

The labelling composition may be selected from the group consisting of and combinations thereof.

The compound may be covalently linked to the protein. The protein may include a polypeptide or an amino acid; or an amino acid derivative (e.g., 5-hydroxytryptophan (5-HTP), or L-dihydroxyphenylalanine (L-DOPA), etc.). The amino acid may be a natural or artificial amino acid. The amino acid may be selected from the group consisting of glycine, alanine, proline, valine, leucine, isoleucine, methionine, serine, threonine, cysteine, selenocysteine, asparagine, glutamine, phenylalanine, tyrosine, tryptophan, lysine, arginine, histidine, aspartic acid, glutamic acid, ornithine and combinations thereof. Further, the protein may be a protein in a cell. The cell may be a bacteria, plant or animal cell. The animal cell may be, for example, HEK 293 (Human Embryonic Kidney 293) cell, HeLa, Huh7, or MDCK cell.

Further, the labelling agent may bind to a linker molecule. The linker molecule may be, for example, biotin, avidin, streptavidin, HRP, protein A, protein G, antibody or a fragment thereof, Grb2, polyhistidine, $Ni^{2+}$, FLAG tag, or myc tag.

Still another aspect provides a method of labelling a protein, the method including contacting the protein with the labelling agent represented by the above described Chemical Formula 1; and irradiating light to the labelling agent. The protein is the same as described above.

The irradiating light to the labelling agent may form a complex of the labelling agent and the protein by binding of the labelling agent and the protein. The complex of the labelling agent and the protein may be formed by covalent binding of the labelling agent and the protein, and therefore, the complex may be a conjugate. The irradiating light may cause a radical reaction of the labelling agent to form the complex of the labelling agent and the protein.

In a specific embodiment, when Y is —OH or —$NR_{13}R_{14}$, and $R_{13}$ and/or $R_{14}$ are/is —H in the labelling agent, the labelling agent may be converted into a tautomer, i.e., ketone, and binds with the protein by hydrogen bonding. The labelling agent may bind with an amine functional group, a hydroxyl functional group, or a thiol functional group of an amino acid or a peptide in the protein. The binding may be covalent binding. For example, in a specific embodiment, when Y is —OH in the labelling agent, the labelling agent may have a tautomeric form as in the following Reaction Scheme 1. The labelling agent may have a characteristic of inducing chemical bonding with the protein by tautomer equilibrium:

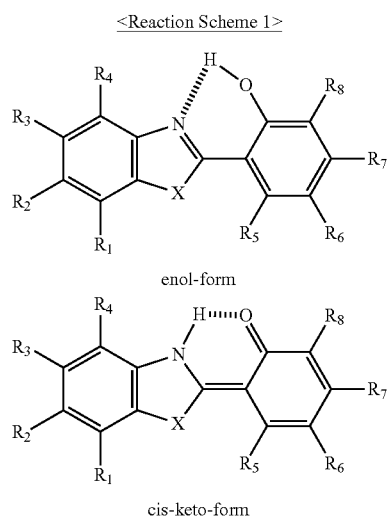

enol-form cis-keto-form

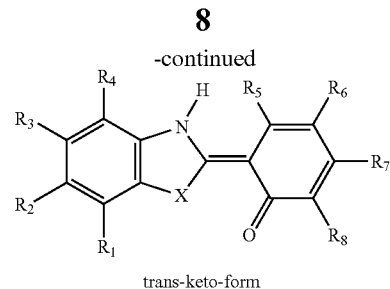

trans-keto-form

The compound may be covalently linked to the protein. The protein may include a polypeptide or an amino acid; or an amino acid derivative (e.g., 5-hydroxytryptophan (5-HTP), or L-dihydroxyphenylalanine (L-DOPA), etc.). The amino acid may be a natural or artificial amino acid. The amino acid may be selected from the group consisting of glycine, alanine, proline, valine, leucine, isoleucine, methionine, serine, threonine, cysteine, selenocysteine, asparagine, glutamine, phenylalanine, tyrosine, tryptophan, lysine, arginine, histidine, aspartic acid, glutamic acid, ornithine and combinations thereof. Further, the protein may be a protein in a cell. The cell may be a bacteria, plant or animal cell. The animal cell may be, for example, HEK 293 (Human Embryonic Kidney 293) cell, HeLa, Huh7, or MDCK cell.

Still another aspect provides a method of labelling a protein, the method including contacting the protein with the labelling agent represented by the above described Chemical Formula 1; and irradiating light to the labelling agent. The protein is the same as described above.

The irradiating light to the labelling agent may form a complex of the labelling agent and the protein by binding of the labelling agent and the protein. The complex of the labelling agent and the protein may be formed by covalent binding of the labelling agent and the protein, and therefore, the complex may be a conjugate.

In a specific embodiment, when Y is —OH or —$NR_{13}R_{14}$, and $R_{13}$ and/or $R_{14}$ are/is —H in the labelling agent, the labelling agent may be converted into a tautomer, i.e., ketone and binds with the protein by hydrogen bonding. The labelling agent may bind with an amine functional group, a hydroxyl functional group, or a thiol functional group of an amino acid or peptide in the protein. Further, the compound may covalently bind to nitrogen at the N-terminus of the amino acid. The binding may be covalent binding. For example, in a specific embodiment, when Y is —OH in the labelling agent, the labelling agent may have a tautomeric form as in the following Reaction Scheme 1. The labelling agent may have a characteristic of inducing chemical bonding with the protein by tautomer equilibrium:

<Reaction Scheme A>

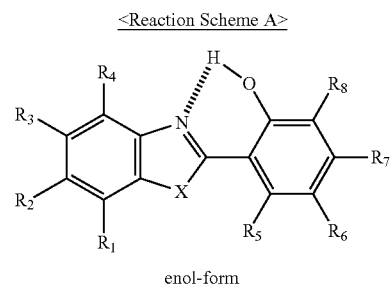

enol-form

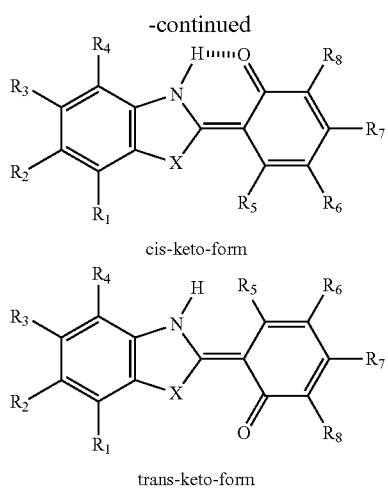

cis-keto-form trans-keto-form

The irradiating light may cause the protein to form a complex with the compound. The irradiating light may be to irradiate light to the mixture of the compound and the protein, after contacting the compound with the protein.

The irradiating light may be performed for fluorescence excitation. The light may have a wavelength of, for example, 200 nm to 400 nm, 200 nm to 350 nm, 200 nm to 300 nm, or 200 nm to 250 nm. The light may be any light, as long as it is emitted from a light source for fluorescence excitation. The light source may be a laser light source. The light may be ultraviolet light.

Still another aspect provides a method of detecting a protein, the method including contacting the protein with the labelling agent represented by the above described Chemical Formula 1; and irradiating light to the labelling agent. The protein is the same as described above.

The irradiating light may be performed to bind the labelling agent and the protein, leading to formation of a complex of the labelling agent and the protein. The detecting may be performed by measuring fluorescence or light absorbance which is emitted from the complex of the labelling agent and the protein after irradiating light.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items.

Hereinafter, the present invention will be described in more detail with reference to Examples. However, these Examples are for illustrative purposes only, and the scope of the present invention is not intended to be limited by these Examples.

Example 1

Preparation of Compound

Experimental device, analyzer and reagents used in Examples and comparative experiments are the same as follows. FT-NMR spectroscopy is performed using Bruker Avance 400, and LC/MS analysis is performed using Thermo Dionex ultimate 3000/Velos pro on ion-trap mass spectrometer (ITMS). All reagents purchased from Aldrich are used without additional purification. Whatman filter papers having a diameter of 125 mm are used. Of derivatives used in experiments, 2-(2-Aminophenyl)-1H-benzimidazole) (ABI) is purchased from Aldrich, and NMR analysis and fluorescence/absorbance values are recorded by the method known in the art.

(1) Synthesis of 2-(2-hydroxyphenyl)benzothiazole (HBT)

Salicylaldehyde (122 mg, 1 mmol, Aldrich) and 2-aminothiophenol (135 ul, 1 mmol, Aldrich) are dissolved in 2 ml of DMF. Under stirring at room temperature, 1 mmol of sodium metabisulfite dissolved in 500 ul of water is added thereto, and allowed to react at 90° C. for about 4 hours. After completion of the reaction, the mixture is precipitated in ice water, and filtered and dried at room temperature. The compound thus dried is dissolved in ethanol, followed by recrystallization (see Lingyu Zeng, Shiyu Chen, Tian Xia, Cheng Zhong and Zhihong Liu. Chem. Commun., 2014, 50, 11139-11142). As described above, HBT is synthesized by the following Reaction Scheme 1.

<Reaction Scheme 1>

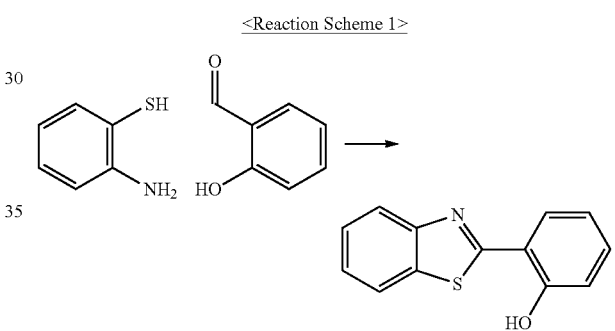

(2) Synthesis of 2-(2-hydroxyphenyl)benzimidazole (HBI)

Salicylaldehyde (122 mg, 1 mmol, Aldrich) and o-phenylenediamine (108 mg, 1 mmol, Aldrich) are dissolved in 2 ml of DMF. Under stirring at room temperature, 1 mmol of sodium metabisulfite dissolved in 500 ul of water is added thereto, and allowed to react at 90° C. for about 4 hours. After completion of the reaction, the mixture is precipitated in ice water, and filtered and dried at room temperature. The compound thus dried is dissolved in ethanol, followed by recrystallization (see Lingyu Zeng, Shiyu Chen, Tian Xia, Cheng Zhong and Zhihong Liu. Chem. Commun., 2014, 50, 11139-11142). As described above, HBI is synthesized by the following Reaction Scheme 2.

<Reaction Scheme 2>

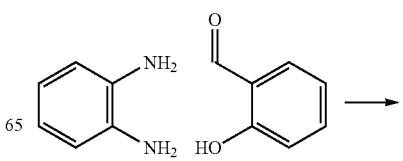

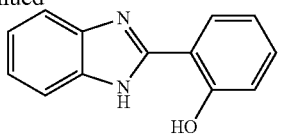

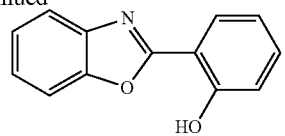

(3) Synthesis of 2-(2-hydroxyphenyl)-5-(diethyl-amino)benzimidazole (HDBI)

4-(Diethylamino)salicylaldehyde) (193 mg, 1 mmol, Aldrich) and o-phenylenediamine (108 mg, 1 mmol, Aldrich) are dissolved in 2 ml of DMF. Under stirring at room temperature, 1 mmol of sodium metabisulfite dissolved in 500 ul of water is added thereto, and allowed to react at 90° C. for about 4 hours. After completion of the reaction, the mixture is precipitated in ice water, and filtered and dried at room temperature. The compound thus dried is dissolved in ethanol, followed by recrystallization (see Lingyu Zeng, Shiyu Chen, Tian Xia, Cheng Zhong and Zhihong Liu. Chem. Commun., 2014, 50, 11139-11142). As described above, HDBI is synthesized by the following Reaction Scheme 3.

<Reaction Scheme 3>

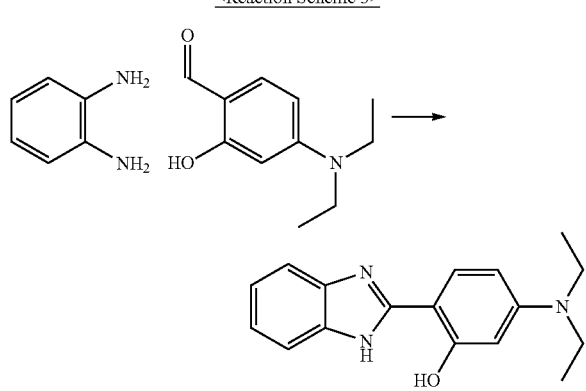

(4) Synthesis of 2-(2-hydroxyphenyl)benzoxazole (HBO)

Salicylaldehyde (122 mg, 1 mmol, Aldrich) and 2-aminophenol (109 mg, 1 mmol, Aldrich) are dissolved in 2 ml of DMF. Under stirring at room temperature, 1 mmol of sodium metabisulfite dissolved in 500 ul of water is added thereto, and allowed to react at 90° C. for about 4 hours. After completion of the reaction, the mixture is precipitated in ice water, and filtered and dried at room temperature. The compound thus dried is dissolved in ethanol, followed by recrystallization (see Lingyu Zeng, Shiyu Chen, Tian Xia, Cheng Zhong and Zhihong Liu. Chem. Commun., 2014, 50, 11139-11142). As described above, HBO is synthesized by the following Reaction Scheme 4.

<Reaction Scheme 4>

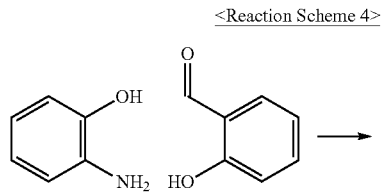

(5) Preparation of 2-(2-Aminophenyl)-1H-benzimidazole (ABI)

2-(2-Aminophenyl)-1H-benzimidazole (ABI) is commercially purchased from Aldrich, and its catalog number is 642681. Chemical Formula of ABI is as follows:

(Formula 4)

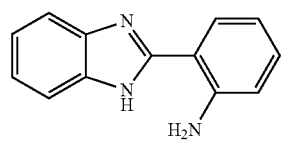

Example 2

Labelling of Protein with Compounds of Example 1

Proteins of BSA, HSA, peroxidase, and lysozyme are treated with the compounds synthesized or purchased in Example 1, and irradiated with UV at about 254 nm. Then, binding of the compound and the protein over UV irradiation time is examined by gel electrophoresis. A gel electrophoresis apparatus (Bio-Rad) and a small vertical gel electrophoresis apparatus are connected and used for gel electrophoresis. For experiment, a 12% SDS gel and a running buffer are directly prepared as follows and used. 12% SDS gel is prepared by mixing 7.9 ml of $H_2O$, 6.5 ml of pH 8.8-50 M Tris-HCl buffer, 10 ml of 30% Acryl amide, 250 μl of 10% SDS gel, 250 μl of APS, and 10 μl of TMEDE. 1× running buffer is prepared by mixing 200 ml of 10×TGS buffer and 1800 ml of $H_2O$.

Proteins of BSA, HAS, peroxidase, and lysozyme are purchased from Sigma Aldrich. Fluorescence intensity of the labeled protein is measured using BIO-RAD ChemiDoc, and Blue Epi and Green Epi are used as a light source, and 530 nm emission (28 nm bandwidth) and 650 nm emission (50 nm bandwidth) filters are used according to fluorescence wavelength.

Table 1 shows maximum values of absorbance and fluorescence of the compounds in DMSO (see Lingyu Zeng, Shiyu Chen, Tian Xia, Cheng Zhong and Zhihong Liu. Chem. Commun., 2014, 50, 11139-11142; Cristina Rodríguez-Rodríguez et al., J. AM. CHEM. SOC. 2009, 131, 1436-1451). When UV at 254 nm is irradiated, they are stable without changes in fluorescence and absorbance. Therefore, the compounds are stable without change in fluorescence even in the absence of a target such as proteins.

TABLE 1

| Compound | Absorbance (nm) | Fluorescence (nm) |
|---|---|---|
| HBT | 350 | 515 |
| HBI | 320 | 463 |

TABLE 1-continued

| Compound | Absorbance (nm) | Fluorescence (nm) |
|---|---|---|
| HDBI | 360 | 448 |
| HBO | 380 | 480 |
| ABI | 360 | 415 |

FIGS. 1a through 1d shows labeling of BSA, HAS, peroxidase, or lysozyme proteins with HBI, HDBI, or HBO of the compounds, and protein labeling efficiency over UV irradiation time. Y axis of FIGS. 1a through 1d represents fluorescence intensity, indicating photocrosslinking degree of the compound and protein.

FIG. 1a shows values of HBI, HDBI, and HBO in this order. As shown in FIG. 1a, significant labeling is observed at 5 minutes after UV irradiation, indicating that BSA is labeled with the compounds only by UV irradiation, and each of the compounds has photocrosslinking property. Therefore, the compounds may be used as a labelling agent, and also as a photocrosslinking agent.

Figure 1B:
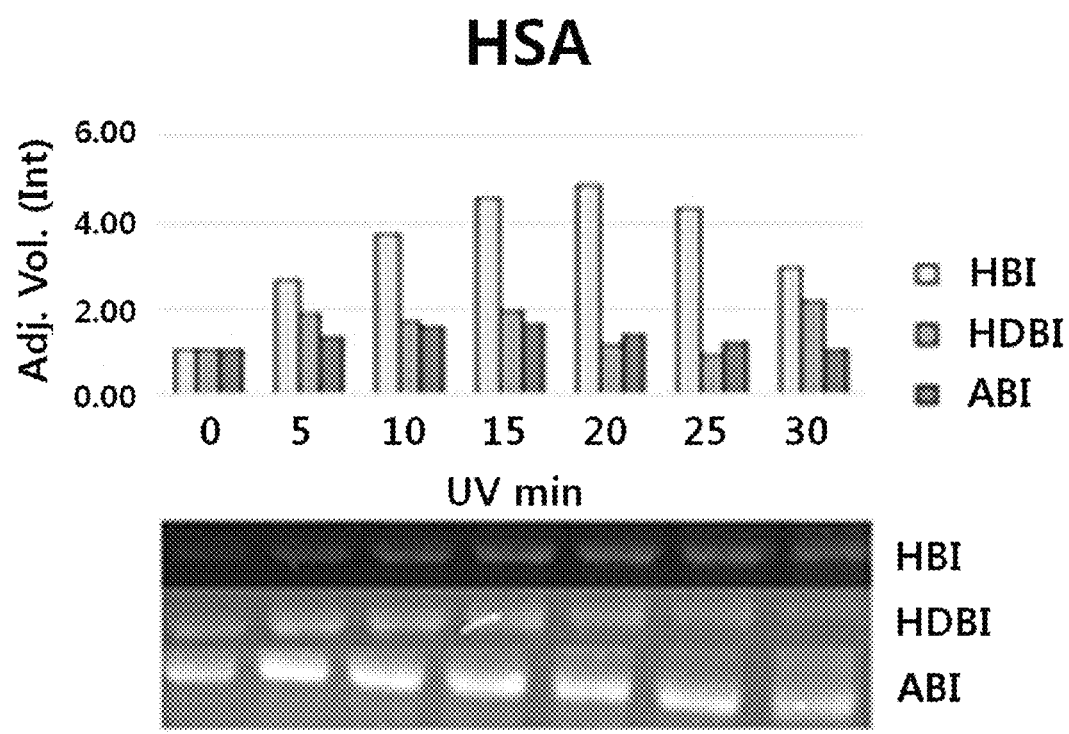

FIG. 1b shows values of HBI, HDBI, and ABI in this order. As shown in FIG. 1b, significant labeling is observed at 5 minutes after UV irradiation, indicating that HSA is labeled with the compounds only by UV irradiation, and each of the compounds has photocrosslinking property. Therefore, the compounds may be used as a labelling agent, and also as a photocrosslinking agent.

Figure 1C:
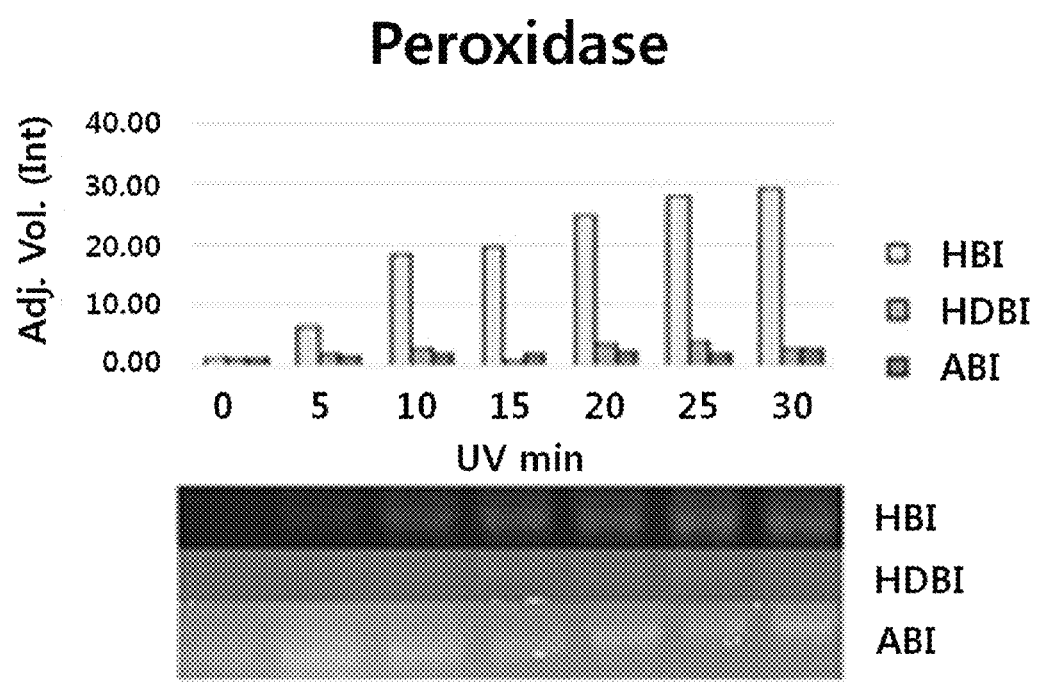

FIG. 1c shows values of HBI, HDBI, and ABI in this order. As shown in FIG. 1c, significant labeling is observed at 5 minutes after UV irradiation, indicating that peroxidase is labeled with the compounds only by UV irradiation, and each of the compounds has photocrosslinking property. Therefore, the compounds may be used as a labelling agent, and also as a photocrosslinking agent.

Figure 1D:
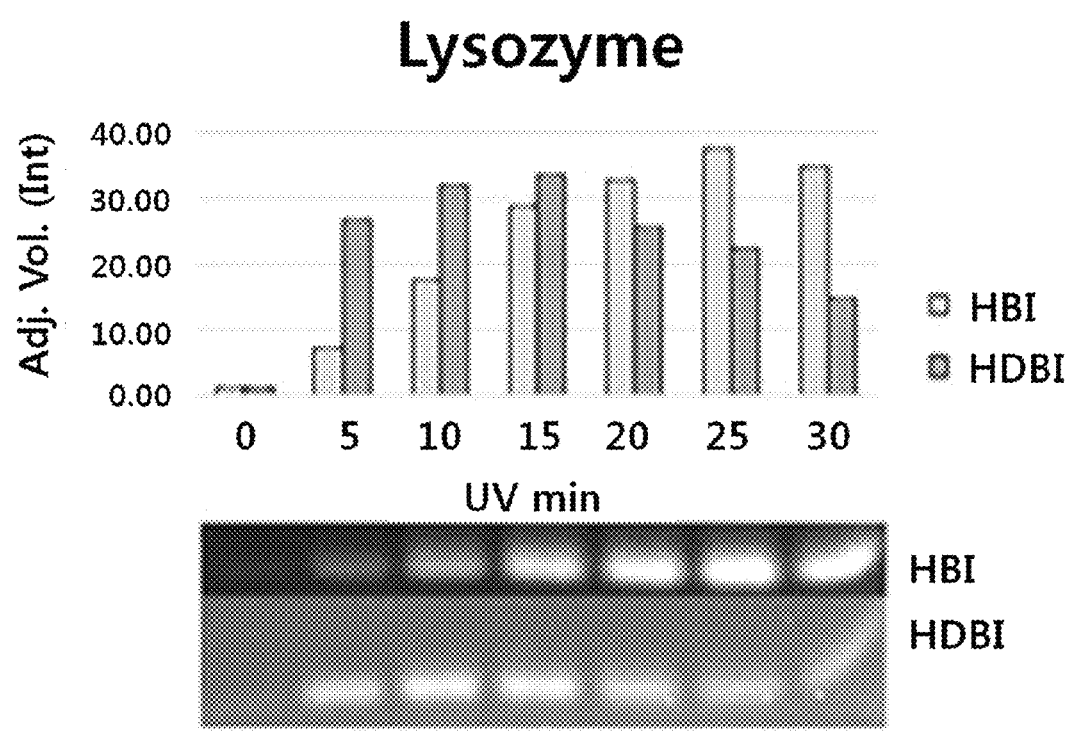

FIG. 1d shows values of HBI and HDBI in this order. As shown in FIG. 1d, significant labeling is observed at 5 minutes after UV irradiation, indicating that lysozyme is labeled with the compounds only by UV irradiation, and each of the compounds has photocrosslinking property. Therefore, the compounds may be used as a labelling agent, and also as a photocrosslinking agent.

The results of FIGS. 1a to 1d taken together, respective HBI, HDBI, and ABI may be used as a protein labelling agent, and these compounds may be used to label proteins only by light irradiation. The compounds may be also used as a photocrosslinking agent. In particular, HBI exhibits the highest photocrosslinking property among the compounds according to a specific embodiment of the present invention.

It should be understood that exemplary embodiments described herein should be considered in a descriptive sense only and not for purposes of limitation.

Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A labelling composition comprising a compound of the following Formula 2 or 3;

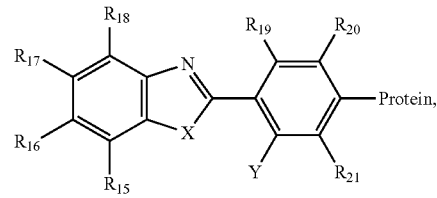

(Formula 2)

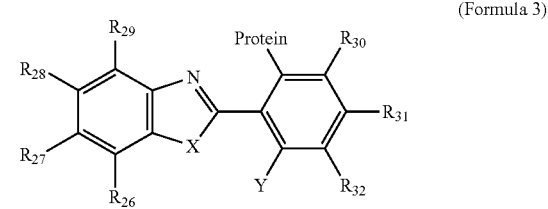

(Formula 3)

wherein $R_{15}$, $R_{16}$, $R_{17}$, $R_{18}$, $R_{19}$, $R_{20}$, and $R_{21}$ are independently H, substituted or unsubstituted —$C_{1-10}$-alkyl-, —$C_{2-10}$-alkenyl, or —$C_{2-10}$-alkynyl, X is —$NR_{22}$, —O, or S, $R_{22}$ is H, substituted or unsubstituted —$C_{1-10}$-alkyl-, —$C_{2-10}$-alkenyl, or —$C_{2-10}$-alkynyl, Y is —$OR_{23}$ or —$NR_{24}R_{25}$, $R_{23}$ is H, substituted or unsubstituted —$C_{1-10}$-alkyl-, —$C_{2-10}$-alkenyl, or —$C_{2-10}$-alkynyl, and $R_{24}$ and $R_{25}$ are independently H, substituted or unsubstituted —$C_{1-10}$-alkyl-, —$C_{2-10}$-alkenyl, or —$C_{2-10}$-alkynyl; and $R_{26}$, $R_{27}$, $R_{28}$, $R_{29}$, $R_{30}$, and $R_{32}$ are independently H, substituted or unsubstituted —$C_{1-10}$-alkyl-, —$C_{2-10}$-alkenyl, or —$C_{2-10}$-alkynyl, $R_{31}$ is —$NR_{32}R_{33}$, $R_{32}$ and $R_{33}$ are independently H, substituted or unsubstituted —$C_1$-10-alkyl-, —$C_{2-10}$-alkenyl, or —$C_{2-10}$-alkynyl, X is —$NR_{34}H$, —O, or S, $R_{34}$ is H, substituted or unsubstituted —$C_{1-10}$-alkyl-, —$C_{2-10}$-alkenyl, or —$C_{2-10}$-alkynyl, Y is —$CR_{35}$ or —$NR_{36}R_{37}$, $R_{35}$ is H, substituted or unsubstituted —$C_{1-10}$-alkyl-, —$C_{2-10}$-alkenyl, or —$C_{2-10}$-alkynyl, and $R_{36}$ and $R_{37}$ are independently H, substituted or unsubstituted —$C_{1-10}$-alkyl-, —$C_{2-10}$-alkenyl, or —$C_{2-10}$-alkynyl.

2. The composition of claim 1, wherein the composition is selected from the group consisting of

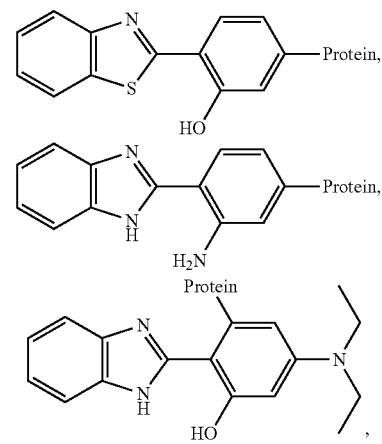

-continued

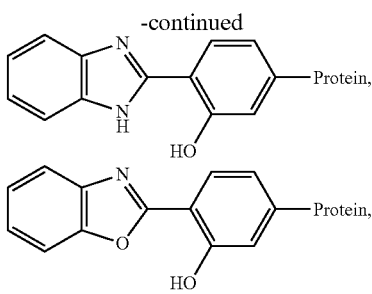

and combinations thereof.

3. A method of labelling a protein, the method comprising:
contacting a protein with a labelling agent represented by the following Chemical Formula 1; and
irradiating light to the labelling agent:

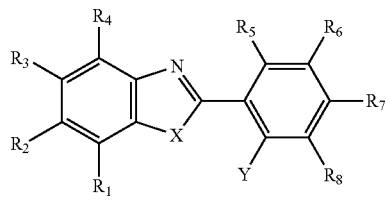

(Formula 1)

wherein $R_1$, $R_2$, $R_3$, $R_4$, $R_5$, $R_6$, and $R_8$ are independently H, substituted or unsubstituted —$C_{1-10}$-alkyl-, —$C_{2-10}$-alkenyl, or —$C_{2-10}$-alkynyl, $R_7$ is H or —$NR_9R_{10}$, $R_9$ and $R_{10}$ are independently H, substituted or unsubstituted —$C_{1-10}$-alkyl-, —$C_{2-10}$-alkenyl, or —$C_{2-10}$-alkynyl, X is —$NR_{11}$, —O, or S, $R_{11}$ is H, substituted or unsubstituted —$C_{1-10}$-alkyl-, —$C_{2-10}$-alkenyl, or —$C_{2-10}$-alkynyl, Y is —$OR_{12}$ or —$NR_{13}R_{14}$, $R_{12}$ is H, substituted or unsubstituted —$C_{1-10}$-alkyl-, —$C_{2-10}$-alkenyl, or —$C_{2-10}$-alkynyl, and $R_{13}$ and $R_{14}$ are independently H, substituted or unsubstituted —$C_{1-10}$-alkyl-, —$C_{2-10}$-alkenyl, or —$C_{2-10}$-alkynyl.

4. The method of claim 3, wherein the irradiating light causes a radical reaction of the labelling agent to form a complex of the labelling agent and the protein.

5. A method of detecting a protein, the method comprising:
contacting a protein with a labelling agent represented by the following Chemical Formula 1; and
irradiating light to the labelling agent:

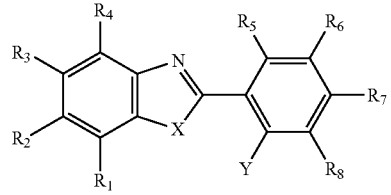

(Formula 1)

wherein $R_1$, $R_2$, $R_3$, $R_4$, $R_5$, $R_6$, and $R_8$ are independently H, substituted or unsubstituted —$C_{1-10}$-alkyl-, —$C_{2-10}$-alkenyl, or —$C_{2-10}$-alkynyl, $R_7$ is H or —$NR_9R_{10}$, $R_9$ and $R_{10}$ are independently H, substituted or unsubstituted —$C_{1-10}$-alkyl-, —$C_{2-10}$-alkenyl, or —$C_{2-10}$-alkynyl, X is —$NR_{11}$, —O, or S, $R_{11}$ is H, substituted or unsubstituted —$C_{1-10}$-alkyl-, —$C_{2-10}$-alkenyl, or —$C_{2-10}$-alkynyl, Y is —$OR_{12}$ or —$NR_{13}R_{14}$, $R_{12}$ is H, substituted or unsubstituted —$C_{1-10}$-alkyl-, —$C_{2-10}$-alkenyl, or —$C_{2-10}$-alkynyl, and $R_{13}$ and $R_{14}$ are independently H, substituted or unsubstituted —$C_{1-10}$-alkyl-, —$C_{2-10}$-alkenyl, or —$C_{2-10}$-alkynyl.

* * * * *